(12) United States Patent
Chen et al.

(10) Patent No.: US 7,914,485 B2
(45) Date of Patent: *Mar. 29, 2011

(54) MEDICAL DEVICE EMPLOYING LIQUID CRYSTAL BLOCK COPOLYMERS AND METHOD OF MAKING THE SAME

(75) Inventors: John J. Chen, Plymouth, MN (US); Joseph Delaney, Jr., Ben Eindhoven (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/549,743

(22) Filed: Aug. 28, 2009

(65) Prior Publication Data

US 2010/0016941 A1 Jan. 21, 2010

Related U.S. Application Data

(63) Continuation of application No. 11/542,856, filed on Oct. 4, 2006, now Pat. No. 7,582,078, which is a continuation-in-part of application No. 11/353,606, filed on Feb. 14, 2006, now Pat. No. 7,662,129.

(51) Int. Cl.
*A61M 25/10* (2006.01)
*B29D 22/00* (2006.01)
*C09K 19/38* (2006.01)

(52) U.S. Cl. ........... 604/96.01; 604/103.01; 604/103.03; 604/524; 428/35.7; 252/299.01

(58) Field of Classification Search ............. 252/299.01; 604/96.01, 103.01, 103.3, 524; 264/171.24; 428/35.7

See application file for complete search history.

(56) References Cited

U.S. PATENT DOCUMENTS

| | | | |
|---|---|---|---|
| 3,778,410 A | 12/1973 | Kuhfuss et al. | |
| 3,804,805 A | 4/1974 | Kuhfuss et al. | |
| 4,238,599 A | 12/1980 | Langley et al. | |
| 4,490,421 A | 12/1984 | Levy | |
| 4,663,422 A | 5/1987 | Inoue et al. | |
| 4,801,677 A | 1/1989 | Eckhardt et al. | |
| 4,912,193 A | 3/1990 | Dicke et al. | |
| 4,952,334 A | 8/1990 | Hakemi et al. | |
| 5,017,304 A | 5/1991 | Hijikata | |
| 5,030,703 A | 7/1991 | Pielartzik et al. | |
| 5,156,785 A | 10/1992 | Zdrahala | |
| 5,173,562 A | 12/1992 | Wilson et al. | |
| 5,248,305 A | 9/1993 | Zdrahala | |
| 5,346,970 A | 9/1994 | Dashevsky et al. | |
| 5,508,338 A | 4/1996 | Kim et al. | |
| 5,565,530 A | 10/1996 | Hattori et al. | |
| 5,677,394 A | 10/1997 | Bohme et al. | |
| 5,750,626 A | 5/1998 | Shimizu et al. | |
| 5,767,198 A | 6/1998 | Shimizu et al. | |
| 5,869,574 A | 2/1999 | Shimizu et al. | |
| 6,024,722 A | 2/2000 | Rau et al. | |
| 6,027,516 A | 2/2000 | Kolobow et al. | |
| 6,054,537 A | 4/2000 | Shimizu et al. | |
| 6,124,007 A | 9/2000 | Wang et al. | |
| 6,132,819 A | 10/2000 | Ober et al. | |
| 6,242,063 B1 | 6/2001 | Ferrera et al. | |
| 6,284,333 B1 | 9/2001 | Wang et al. | |
| 6,325,780 B1 | 12/2001 | Schaible et al. | |
| 6,328,925 B1 | 12/2001 | Wang et al. | |
| 6,443,925 B1 | 9/2002 | Schaible et al. | |
| 6,552,127 B1 | 4/2003 | Shimizu et al. | |
| 6,596,219 B2 | 7/2003 | Schaible et al. | |
| 6,730,377 B2 | 5/2004 | Wang | |
| 6,790,908 B2 | 9/2004 | Bendejacq et al. | |
| 6,905,743 B1 | 6/2005 | Chen et al. | |
| 6,930,166 B2 | 8/2005 | Yamamoto | |
| 6,977,103 B2 | 12/2005 | Chen et al. | |
| 6,986,785 B2 | 1/2006 | O'Shaughnessy et al. | |
| 7,026,026 B2 | 4/2006 | Ferrera et al. | |
| 7,101,597 B2 | 9/2006 | Wang et al. | |
| 7,582,078 B2 * | 9/2009 | Chen et al. | 604/524 |
| 7,662,129 B2 * | 2/2010 | Chen | 604/96.01 |
| 2001/0019751 A1 | 9/2001 | Ferrera et al. | |
| 2005/0142314 A1 | 6/2005 | Burgmeier et al. | |
| 2005/0182473 A1 | 8/2005 | Eidenschink et al. | |
| 2006/0008606 A1 | 1/2006 | Horn et al. | |
| 2007/0191813 A1 | 8/2007 | Chen | |
| 2010/0145269 A1 * | 6/2010 | Chen | 604/96.01 |

FOREIGN PATENT DOCUMENTS

JP 10007779 1/1998

(Continued)

OTHER PUBLICATIONS

X. Han et al., "Synthesis and Characterization of Side-Chain Liquid Crystalline Poly[1-({[4-cyano-4'-diphenyl)oxy]alkyl}oxy)2,3-epoxypropane]", Macromolecular Chemistry and Physics, vol. 205, pp. 743-751 (2004).
P. Gopalan et al., "Rod-Coil Block Copolymers: An Iterative Synthetic Approach via Living Free-Radical Procedures," Journal of Polymer Science: Part A: Polymer Chemistry, vol. 41, pp. 3640-3656 (2003).
Hakemi, H., "On the miscibility of liquid crystalline polymers," Polymer, vol. 41, pp. 6145-6150 (2000).
B.L. Rivas et al., "Synthesis and Characterization of Block Copolymers from Poly(p-benzamide) and Poly(propylene glycol)," Macromolecular Chemistry and Physics, vol. 202, pp. 1053-1059 (2001).
Ober et al. in "Liquid Crystal Polymers. V. Thermotropic Polyesters with Either Dyad or Triad Aromatic Ester Mesogenic Units and Flexible Polymethylene Spacers in the Main Chain," Polymer Journal, vol. 14, No. 1, pp. 9-17 (1982).

(Continued)

*Primary Examiner* — Shean C Wu
(74) *Attorney, Agent, or Firm* — Vidas, Arrett & Steinkraus, P.A.

(57) ABSTRACT

A medical device, at least a portion of which is formed from a polymer composition including at least one liquid crystal block copolymer having at least one A block and at least one B block wherein the A block is a liquid crystal polymer block formed of repeating units comprising mesogenic groups and the B block is a non-liquid crystal polymer block.

20 Claims, No Drawings

FOREIGN PATENT DOCUMENTS

| WO | 9748782 | 12/1997 |
|---|---|---|
| WO | 9932576 | 7/1999 |
| WO | 02056930 | 7/2002 |
| WO | 2006068712 | 6/2006 |

OTHER PUBLICATIONS

He et al., "Synthesis of side-chain liquid-crystalline homopolymers and triblock copolymers with p-methoxyazobenzene moieties and poly(ethylene glycol) as coil segments by atom transfer radical polymerization (ATRP) and their thermotropic behavior," Journal of Polymer Science Part A: Polymer Chemistry, vol. 41, Issue 18, pp. 2854-2864 (2003).

Gomes et al., "Synthesis of block and graft copolymers containing liquid-crystalline segments," Polymer International, vol. 48, pp. 713-722 (1999).

P. Ravi et al., "New water soluble azobenzene-containing diblock copolymer: synthesis and aggregation behavior," Polymer, vol. 46, pp. 137-146 (2005).

Cui et al., "Photoactive Thermoplastic Elastomers of Azobenzene-Containing Triblock Copolymers Prepared through Atom Transfer Radical Polymerization," Macromolecules, vol. 37, pp. 7097-7104 (2004).

Han et al., "Synthesis and Characterization of New Liquid-Crystalline Block Copolymers with p-Cyanoazobenzene Moieties and poly(n-butyl acrylate) segments Using Atom-Transfer Radical Polymerization," Macromolecules, vol. 37, pp. 9355-9365 (2004).

Yamada et al., "Synthesis of Side-Chain Liquid Crystalline Homopolymers and Block Copolymers with Well-Defined Structures by Living Anionic Polymerization and Their Thermotropic Phase Behavior," Macromolecules, vol. 28, pp. 50-58 (1995).

Yamada et al., "Side-Chain LC Block Copolymers with Well Defined Structures Prepared by Living Anionic Polymerization 2: Effect of the Glass Transition Temperature of Amorphous Segments on the Phase Behaviour and Structure of the LC Segment," High Performance Polymers, vol. 10(1), pp. 131-138 (1998).

Barbosa et al., "Living tandem free radical polymerization of a liquid crystalline monomer," Polymer Bulletin, vol. 41, pp. 15-20 (1998).

Hamley et al., "Interplay between Smectic Ordering and Microphase Separation in a Series of Side-Group Liquid-Crystal Block Copolymers," Macromolecules, vol. 37, pp. 4798-4807 (2004).

Tian et al., "Photocrosslinkable Liquid-Crystalline Block Copolymers with Coumarin Units Synthesized with Atom Transfer Radical Polymerization," Journal of Polymer Science: Part A: Polymer Chemistry, vol. 41, pp. 2197-2206 (2003).

Hao et al., "Molecular composite materials formed from block copolymers containing a side-chain liquid crystalline segment and an amorphous styrene-alt-maleic anhydride segment," Polymer, vol. 45, pp. 7401-7415 (2004).

Wan et al., "Nitroxide-mediated 'living' free radical sythesis of novel rod-coil diblock copolymers with polystyrene and mesogen-jacketed liquid crystal polymer segments," Polymer International, vol. 49, pp. 243-247 (2000).

Moments et al., "Synthesis of polystyrene-polysiloxane side-chain liquid crystalline block copolymers," Macromolecular Rapid Communications, vol. 19, pp. 573-579 (1998).

Huan et al., "Synthesis and Properties of Polydimethylsiloxane-Containing Block Copolymers via Living Radical Polymerization," Journal of Polymer Science: Part A: Polymer Chemistry, vol. 39, pp. 1833-1842 (2001).

M.C. Bignozzi et al., "Liquid Crystal Poly(glycidyl ether)s by Anionic Polymerization and Polymer-Analogous Reaction," Polymer Journal, vol. 31, No. 11-1, pp. 913-919 (1999).

C. Guillermain et al., "Homopolymers and copolymers of Nε-4-phenylbenzamido-L-lysine and Nε-trifluroracetyl-L-lysine: Synthesis and liquid-crystaline properties," Macromolecular Chemistry and Physics, vol. 203, Issue 10-22, pp. 1346-1356 (2002).

Rodriguez-Parada et al., "Synthesis and Characterization of Liquid Crystalline Poly(N-acelyethyleneimine)s," Journal of Polymer Science: Part A, Polymer Chemistry, vol. 25, 2269-2279 (1987).

Jun-Hwan Ahn et al., "Synthesis of well-defined block copolymers of n-hexyl isocyanate with isoprene by living anionic polymerization," Polymer 44, pp. 3847-3854 (2003).

Man et al., "Molecular Design, Synthesis, and Characterization of Liquid Crystal-Coil Diblock copolymers with Azobenzene Side Groups, Macromolecules," vol. 30, pp. 2556-2567 (1997).

Bignozzi et al., "Liquid crystalline side chain-coil diblock copolymers by living free radical polymerization," Macromolecular Rapid Communications, vol. 20, pp. 622-627 (1999).

J. Wang et al., "Liquid Crystalline, Semifluorinated Side Group Block Copolymers with Stable Low energy Surfaces: Synthesis, Liquid Crystalline Structure, and Critical Surface Tension," Macromolecules, vol. 30, pp. 1906-1914 (1997).

Al-Hussein et al., "Nanoordering of Fluorinated Side-Chain Liquid Crystalline/Amorphous Diblock Copolymers, Macromolecules," vol. 38, pp. 9610-9618 (2005).

Chen et al., "Synthesis and Characterization of Novel Mesogen-Jacketed Liquid Crystalline Miktoarm Star Rod-Coil Block Copolymer," Macromolecular Rapid Communications, vol. 27, pp. 51-56 (2006).

Wang et al., "Synthesis of a Novel Liquid Crystal Rod-Coil Star Block Copolymer Consisting of Poly(methyl methacrylate) and Poly{2,5-bis[(4-methoxy-phenyl)oxycarboyl] styrene} via Atom Transfer Radical Polymerization," Journal of Polymer Science: Part A: Polymer Chemistry, vol. 43, pp. 733-741 (2005).

Wang et al., "Synthesis and characterization of four-armed star mesogen-jacketed liquid crystal polymer," Journal of Polymer Science: Part A: Polymer Chemistry, vol. 45, pp. 3637-3642 (2004).

Shi et al., "Synthesis and Characterization of a novel star shaped Rod-Coil Block Copolymer," Polymer Bulletin, vol. 52, pp. 401-408 (2004).

Wang et al., "Synthesis of a novel star liquid crystal polymer using trifunctional initiator via atom transfer radical polymerization," European Polymer Journal, vol. 41, pp. 933-940 (2005).

He et al., "Synthesis of novel multi-arm star azobenzene side-chain liquid crystalline copolymers with a hyperbranched core," European Polymer Journal, vol. 40, pp. 1759-1765 (2004).

He et al. "Branched Azobenzene Side-Chain Liquid-Crystalline Copolymers Obtained by Self-Condensing ATR Copolymerization," Macromolecular Rapid Communications, vol. 25, pp. 949-953 (2004).

He et al., "Synthesis of side-chain liquid-crystalline homopolymers and triblock copolymers with p-methoxyazobenzene moieties and poly(ethylene glycol) as coil segments by atom transfer radical polymerization and their thermotropic phase behavior," Journal of Polymer Science Part A: Polymer Chemistry, vol. 41, Issue 18, pp. 2854-2864 (2003).

He et al., "Synthesis of Side Chain Liquid Crystal-Coil Diblock Copolymers with p-Methoxyazobenzene Side Groups by Atom-Transfer Radical Polymerization (structure V)", Polymer Chemistry, vol. 41, 2854-2864 (2003).

Tian et al., "Synthesis, Nanostructures, and Functionality of Amphiphilic Liquid Crystalline Block Copolymers with Azobenzene Moieties," Macromolecules, vol. 35, pp. 3739-3747 (2002).

He et al., "Synthesis of side group liquid crystal-coil triblock copolymers with cyanodiphenyl moieties and PEG as coil segments by atom-transfer radical polymerization and their thermotropic phase behavior," Polymer Bulletin, vol. 48, pp. 337-344 (2002).

Chen et al, "Synthesis and properties of liquid crystalline polymers with low Tm and broad mesophase temperature ranges," Polymer, 46 (2005) 8624-8633.

Hurdoc, Nicolae, et al., "Thermal Behaviour and Molecular Modeling of Some Aromatic Polyethers Containing a Hexamethylenic Spacer," Polymer Degradation and Stability, 72 (2001), 441-445.

Liu, Yingliang, et al., "Synthesis and Characterization of Liquid Crystalline Copolyesters Containing Horizontal and Lateral Rods in Main Chain (II)," Reactive & Functional Polymers, 64 (2005) 35-46.

Makaruk, Leszek, et al., "Mesophase Transitions in Liquid Crystal Polymers," Reactive & Functional Polymers, 33 (1997) 225-231.

http://www.sharpsma.com/lcd/lcdguide/Primer/crystal-intro.php, "Liquid Crystal Physics" pp. 1-3.

http://www.cem.msu.edu/~reusch/VirtualText/polymers.htm, "Polymers" pp. 1-19.

http://plc.cwru.edu/tutorial/enhanced/files/plc/mc_plc/MC_plc.htm, "Main Chain Polymer Liquid Crystals" pp. 1-2.
http://en.wikipedia.org/wiki/Mesogen, "Mesogen" pp. 1.
Zheng et al., "Synthesis of new smectic C* liquid-crystalline block copolymers," Macromol. Rapid Commun., 17, 813-824 (1996).
Yi et al., "Synthesis of Novel Hybrid Liquid-Crystalline Rod-Coil Diblock Copolymer," Journal of Polymer Science: Part A: Polymer Chemistry, vol. 41, 1799-1806 (2003).
Li et al., "Liquid-Crystalline Polymethacrylates by Atom-Transfer Radical Polymerization at Ambient Temperature," Macromol. Chem. Phys. pp. 619-626, 2002, 203, No. 4.

Serhatli et al., "Synthesis of Liquid Crystalline-Amorphous Block Copolymers by Combination of CFRP-ATRP Mechanisms," Journal of Applied Polymer Science, vol. 99, 3187-3194 (2006).
Mruk et al., "Amphotrophic Ionomers by Attachment of Secondary Amines to a Reactive Ester Polymer," Macromol. Chem. Phys. 2004, 205, 2169-2174.
Zhang et al., "Synthesis of a Novel ABC Triblock Copolymer with a Rigid-Rod Block via Atom Transfer Radical Polymerization," Macromol. Rapid Commun. 2005, 26, 407-411.

* cited by examiner

MEDICAL DEVICE EMPLOYING LIQUID CRYSTAL BLOCK COPOLYMERS AND METHOD OF MAKING THE SAME

CROSS-REFERENCE TO RELATED APPLICATIONS

This application is a continuation of U.S. patent application Ser. No. 11/542,856 filed Oct. 4, 2006, which is a continuation-in-part of copending U.S. patent application Ser. No. 11/353,606 filed Feb. 14, 2006, all of which are hereby incorporated by reference.

FIELD OF THE INVENTION

The present invention relates to the field of insertable and/or implantable medical devices, particularly to balloon catheter assemblies and components thereof.

BACKGROUND OF THE INVENTION

It is known to use liquid crystal polymers (LCPs) in combination with thermoplastic polymers, i.e. matrix polymers, for use in the manufacture of insertable and/or implantable medical devices such as catheter assemblies and components thereof such as inflatable medical balloons which can be disposed at the distal end of a balloon catheter assembly. For example, see commonly assigned U.S. Pat. Nos. 6,977,103, 6,905,743, 6,730,377 and 6,284,333. See also U.S. Pat. Nos. 6,596,219, 6,443,925 and 6,325,780 to Schaible.

Liquid crystal polymers are known to phase separate from commonly used thermoplastic polymers into multiphase polymer compositions. For example, see U.S. Pat. Nos. 5,248,305 and 5,156,785 to Zdrahala.

Compatibilized blends of LCP and thermoplastic polymers have been found suitable for use as medical device balloon materials. See for example commonly assigned U.S. Pat. No. 6,242,063.

It would be desirable to have a liquid crystal polymer material or blend using a liquid crystal polymer material which has increased compatibility over other previous LCP/polymer blends which could be employed in the formation of medical devices, particularly in the manufacture of catheter assemblies or components thereof.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

Without limiting the scope of the invention a brief summary of some of the claimed embodiments of the invention is set forth below. Additional details of the summarized embodiments of the invention and/or additional embodiments of the invention may be found in the Detailed Description of the Invention below.

SUMMARY OF THE INVENTION

The present invention relates to polymer compositions useful in the formation of medical devices which include at least one liquid crystal block copolymer having at least one A block and at least one B block.

The A block, which may also be referred to herein as the mesogenic (liquid crystal) block, may include any suitable repeating unit, the repeating unit having mesogenic groups. Any suitable mesogenic repeating unit may be employed herein.

In some embodiments, the A block has at least one aromatic group per each mesogenic repeating unit and more suitably the A block has at least two aromatic groups per each mesogenic repeating unit.

In other embodiments, the mesogenic repeating unit may include fluorocarbon chains. Suitably, the fluorocarbon chain includes at least eight fluorocarbon groups, $—(CF_2)_8—$. A spacer may also be incorporated in the chain. In some embodiments the spacer includes three or less methylene, $—CH_2—$ groups.

The B block may be formed of any suitable repeating unit which does not include mesogenic groups, i.e. the B block is a non-liquid crystal polymer block.

In some embodiments, the B block is aliphatic. Suitably the B block has less than 10% aromaticity by weight of the B block, more suitably less than 5% aromaticity by weight of the B block and most suitably substantially no aromaticity.

In other embodiments, the B block may be aromatic. In some embodiments, the B block is formed of styrenic units.

The polymers may be formed using conventional reaction techniques such as condensation reactions, chemical modification of precursor polymers such as through addition reactions, sequential addition of a first block to a second block, anionic or cationic polymerization, free radical polymerization, coupling end-functionalized prepolymers, ring opening metathesis polymerization, group transfer polymerization, etc., as will be described in more detail below.

These polymers may be employed alone, or in combination with other polymers.

The polymers find particular utility in the formation of medical devices such as catheter assemblies and components thereof, including, for example, shafts, tips, manifolds and balloons.

These and other aspects, embodiments and advantages of the present invention will become immediately apparent to those of ordinary skill in the art upon review of the Detailed Description and Claims to follow.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The present invention relates to polymer compositions useful in the formation of medical devices or at least a portion of a medical device. The polymer compositions include at least one liquid crystal block copolymer having at least one A block and at least one B block.

The A block is formed of mesogenic (liquid crystal) repeating units. As used herein, the term "mesogen" shall be used to refer to those structural groups which impart liquid crystal properties, such as stiffness and restriction to rotation, to the polymer. The term "mesogenic unit" as employed herein, shall be used to refer to any polymer repeating units having a mesogen. Mesogenic groups may include other structure groups, as well as spacers such as methylene groups, and linking groups.

Polymer repeating units include backbone portions which including linking groups and typically an intermediate linear or cyclic structure therebetween. Repeating units often include one or more groups pendent to the backbone polymer chains.

The mesogenic repeating unit of the present application may be said to include both a mesogenic portion and a spacer. Spacers are typically flexible and often include methylene ($—CH_2—$) groups. Flexible spacers have been found to be advantageous when inserted between the polymer backbone and the mesogenic side group, for example, to separate the motion of the polymer backbone. See, for example, X. Han et al., "Synthesis and Characterization of Side-Chain Liquid Crystalline Poly[1-({[4-cyano-4'-diphenyl)oxy]alkyl}oxy)2, 3-epoxypropane]", *Macromolecular Chemistry and Physics*, Vol. 205, pp. 743-751 (2004). The mesogenic repeating units of the A block can be attached together in such a way that the mesogen portion of the mesogenic repeating unit forms a part of the backbone (main chain liquid crystal polymer structure), or they may be attached together in such a way that the mesogen is attached to the polymer backbone as a pendant group (side chain liquid polymer structure). Examples of aromatic mesogenic repeating units employed in main chain liquid crystal polymers wherein the mesogen portion of the mesogenic repeating unit forms a part of the backbone is hydroxynaphthoic acid, and poly(p-phenyleneterephthalate).

Liquid crystals exhibit a phase of matter which exists between a crystalline (solid) and an isotropic (liquid) phase, that has properties between those of a conventional liquid, and those of a solid crystal. For instance, a liquid crystal (LC) may flow like a liquid, but have the molecules in the liquid arranged and oriented in a crystalline way. It is the mesogen of the mesogenic repeating unit which induces the structural order, rigidity and necessary restriction on movement that allows the polymer to display these liquid crystal properties. The mesogen is typically made up of one or more aromatic rings. Suitably, each mesogenic repeating unit has at least one aromatic group per each repeating unit, and more suitably each mesogenic repeating unit has at least two aromatic groups per each repeating unit.

The B block may be either a hard block or a soft block, providing that it is not formed of mesogenic repeating units. The block copolymer may also be of a multiblock variety including C blocks, D blocks, etc. The C block and the D block may be either be non-liquid crystal blocks or liquid crystal blocks. For example, in the case of an ABC block copolymer, the A block may be formed of a first mesogenic repeating unit, the B block may be formed of a non-mesogenic repeating unit, and the C block may be formed of a second mesogenic repeating unit different that the first mesogenic repeating unit. In some embodiments, the B block is immiscible with the A block.

The block copolymers may be of the general formula A-B diblock, A-B-A triblock and B-A-B triblock, polyblock copolymers of the formula $(A-B)_n$ where n is 1 to 20, $A(B-A)_n$ and $B(A-B)_n$ where n is 2 to 20, A-B-A-B-A pentablock, multiblock polymers such as A-B—C, A-C—B or BAC triblock copolymers, $B-(A-B—C)_n$ wherein n is 3 to 20, A-B—C-D multiblock copolymers, random block copolymers and alternating random block copolymers, etc.

Furthermore, branched architecture block copolymers including H-type, T-type, stars (including symmetric and heterobranched stars), combs, brushes, dendrons/hyperbranched, etc. may be employed herein.

Individual polymer blocks of a block copolymer are often referred to in the art as being either a "hard block" or a "soft block", and may be defined in terms of its Tg, the hard block having a relatively high glass transition temperature (Tg) and the soft block having a relatively low Tg. A hard block, for example, may be considered as having a high Tg of greater than room temperature or greater than about 25° C., for example, while a soft block may be considered as having a Tg of less than room temperature or less than about 25° C. However, this is intended for illustrative purposes only. For example, see U.S. Pat. No. 6,790,908, the entire content of which is incorporated by reference herein, wherein the stiff block is defined as having a glass transition temperature of greater than about 50° C., and preferably greater than 100° C.

The A block, which may also be referred to herein as the mesogenic block, may include any suitable mesogenic repeating unit. In some embodiments, the mesogenic repeating unit has at least one aromatic group per unit, and more suitably the mesogenic repeating unit has at least two aromatic groups per unit. The A block of the liquid crystal block copolymer is characterized by mesogenic repeating units which can provide the liquid crystal block copolymer with stiffness resulting from restriction on rotation caused by steric hindrance and resonance. For example, aromatic ring(s) can provide both steric hindrance and resonance. Some mesogenic repeating units may include both aromatic and aliphatic rings.

The A block may contain any number of repeating units up to about 50.

Suitably, the mesogenic block has an axial ratio, defined by the length of the molecule divided by the diameter (x=L/d), of at least three. This axial ratio provides the mesogenic block with rod-like characteristics.

The mesogenic block can be formed using a variety of techniques including, but not limited to, polymerization of mesogenic monomeric repeating units, addition of mesogenic side chain groups to otherwise non-mesogenic blocks followed by sequential addition of the mesogenic block to a non-mesogenic block, chemical modification of a non-mesogenic block copolymer by addition of mesogenic side chain groups, etc.

A variety of methods can be employed in the formation of the LCP block copolymers discussed herein and some of which are discussed in more detail below. Conventional condensation reactions are commonly employed, as well as chemical modification of a precursor polymers such as through addition reactions, anionic and cationic polymerization, free radical polymerization, ring opening metathesis polymerization, coupling end-functionalized pre-polymers, group transfer polymerization, sequential addition of a first block to a second block. See, for example, P. Gopalan et al., "Rod-Coil Block Copolymers: An Iterative Synthetic Approach via Living Free-Radical Procedures," *Journal of polymer Science: Part A: Polymer Chemistry*, Vol. 41, pp. 3640-3656 (2003), Hakemi, H., "On the miscibility of liquid crystalline polymers," *Polymer*, Vol. 41, pp. 6145-6150 (2000), each of which is incorporated by reference herein in its entirety.

Condensation reactions are very common in the preparation of LCP copolymers. Condensation often involves first synthesizing the end-blocks and mid-blocks and subsequently coupling of the end-functionalized prepolymers.

Alternating and random block copolymers have been prepared using condensation reactions. See U.S. Pat. Nos. 3,778, 410 and 3,804,805, the entire contents of which are incorporated by reference herein.

ABA triblocks may also be prepared using condensation techniques. See, for example, B. L. Rivas et al., "Synthesis and Characterization of Block Copolymers from Poly(p-benzamide) and Poly(propylene glycol)," *Macromolecular Chemistry and Physics*, Vol. 202, pp. 1053-1059 (2001).

However, it should be noted that for LC block copolymers formed using condensation mechanisms, some prepolymers may be more suitable for use as end blocks than others due to reactive non-equivalency of the end groups. Suitably, for a prepolymer to act as an effective end-block, one end of the polymer chain should be non-reactive, while the other end should be readily reactive to the endgroups of the other chain. For example, poly(1,-4-phenylene terephthalate) may be less suitable for use as compared to poly(4-benzoate) in formation of LC block copolymers. An example of a condensation polymerization which produces an AB-type condensation polymer and involves a single monomer with two types of reactive end-groups, i.e. 4-hydroxybenzoic acid, or 4-aminobenzoic acid, which yields a condensation product that has endgroups which have non-equivalent reactivity is described by B. L. Rivas et al., "Synthesis and Characterization of Block Copolymers from Poly(p-benzamide) and Poly(propylene glycol)," *Macromolecular Chemistry and Physics*, Vol. 202, pp. 1053-1059 (2001).

Another technique which also may be employed in the formation of condensation block copolymers includes the use of two or more 2,2',6',2"-terpyridine-substituted prepolymers coordinating to a single transition metal center to form block copolymers.

A variety of suitable mesogenic repeating units find utility in the formation of the A block of the liquid crystal block copolymer.

Classes of aromatic structural groups useful in the formation of main chain mesogenic repeating units include, but are not limited to, aromatic dicarboxylic acids, aromatic hydroxycarboxylic acids, aromatic aminocarboxylic acids, diphenols, and aminophenols, for example.

Examples of useful aromatic dicarboxylic acids include, but are not limited to, 1,4-naphthalenedicarboxylic acid, 1,5-naphthalenedicarboxylic acid, 2,6-naphthalenedicarboxylic acid, diphenyl-4,4'-dicarboxylic acid, diphenyl-3,3'-dicarboxylic acid, diphenoxyethane-4,4'-dicarboxylic acid, diphenyl ether-4,4'-dicarboxylic acid, methylterephthalic acid, methoxyterephthalic acid, chloroterephthalic acid, 4-chloronaphthalene-2,7-dicarboxylic acid, 1,3-naphthalenedicarboxylic acid, 1,6-naphthalenedicarboxylic acid, 1,7-naphthalenedicarboxylic acid, 2,7-naphthalenedicarboxylic acid, diphenyl-3,4'-dicarboxylic acid, diphenyl ether-3,4'-dicarboxylic acid, 4-methylisophthalic acid, 5-methylisophthalic acid, diphenyl ether-4,4'-dichloro-3,3'-dicarboxylic acid and iso- and terephthalic acid.

Examples of useful aromatic hydroxycarboxylic acids include, but are not limited to, 4-hydroxy-3-methylbenzoic acid, 4-hydroxy-3-phenyl-benzoic acid, 4-hydroxy-2-ethylbenzoic acid, 3-chloro-4-hydroxy-benzoic acid, 4-hydroxy-3-methoxybenzoic acid, hydroxyl benzoic acid including 4-hydroxybenzoic acid and 3-hydroxybenzoic acid, hydroxynaphthoic acid including 6-hydroxy-2-naphthoic acid, etc.

Examples of useful diphenols include, but are not limited to, hydroquinone, t-butylhydroquinone, bromohydroquinone, chlorohydroquinone, methylhydroquinone, ethylhydroquinone, phenylhydroquinone, 4,4'-dihydroxybiphenyl, 4,4'-dihydroxydiphenyl ether, 4,4'-dihydroxydiphenylethane, 4,4'-dihydroxydiphenoxyethane, 3,5'-dihydroxybiphenyl, 4-hydroxy-4'-carboxybiphenyl, 3,5'-dihydroxydiphenyl ether, naphthalene, dihydroxynaphthalene including 1,4-, 1,5- and 2,6-dihydroxynaphthalene, for example, 4-methoxy-2,6-dihydroxynaphthalene, 1,3-dihydroxynaphthalene, 1,6-dihydroxynaphthalene, 1,7-dihydroxynaphthalene, 2,7-dihydroxynaphthalene, 2,5-dichloro-1,6-dihydroxynaphthalene, 4-methoxy-2,7-dihydroxynaphthalene, 2,2'-dimethyl-4,4'-dihydroxybiphenyl, 3,3',5,5'-tetramethyl-4,4'-dihydroxybiphenyl, 3,5'-dimethoxy-4,4'-dihydroxydiphenyl ether, 1,2-(2-chloro-4-hydroxyphenoxy)-ethane resorcinol, 3,4'-dihydroxybiphenyl, 3,4'-dihydroxydiphenyl ether, 3,4'-dihydroxydiphenoxyethane, 4-chlororesorcinol, 4-bromoresorcinol, 4-methylresorcinol, 4-phenylresorcinol, 4-ethoxyresorcinol, etc.

Examples of aromatic aminocarboxylic acids include, but are not limited to, 2-aminobenzoic acid, 3-aminobenzoic acid, 4-aminobenzoic acid, 4-chloroanthranilic acid, 5-chloroanthranilic acid, 3-amino-4-chlorobenzoic acid, 4-amino-3-phenyl-benzoic acid, 4-amino-3-methoxybenzoic acid, 4-amino-3-phenoxybenzoic acid, 6-amino-5-chloro-2-naphthoic acid, 6-amino-5-methyl-2-naphthoic acid and 6-amino-5-methoxy-2-naphthoic acid, etc.

Examples of aminophenols include, but are not limited to, 3-aminophenol, 5-amino-2-chlorophenol, 4-aminophenol, 3-amino-2-methylphenol, 3-amino-4-methylphenol, 5-amino-1-naphthol, 6-amino-1-naphthol, 8-amino-2-naphthol, 6-amino-2-naphthol and 4-amino-1-hydroxy-biphenyl, etc.

Other mesogenic repeat units not specifically recited herein can be employed. For example, other dihydroxy biphenyls, dicarboxy biphenyls and diamino biphenyls, not specifically recited herein may also find utility in the formation of the LC block copolymers disclosed herein.

Other groups which may be included in a main chain mesogenic repeating unit include paraphenylene (—Ar—) wherein Ar represents an aromatic ring, as well as substituted paraphenylenes such as para-diacetoxyphenylene (—CH$_2$COOCH2-Ar—CH$_2$COOCH$_2$—). Meta-phenylene may also be employed in the mesogenic repeating unit as well.

Other combinations of such groups which may produce mesogenic repeating units may also be incorporated into the repeating unit in the LC block of the LC block copolymer. For a discussion of these structural groups, see for example, U.S. Pat. Nos. 4,663,422, 5,017,304 and 5,030,703 for a discussion of such structural units, each of which is incorporated by reference herein in its entirety. See also U.S. Pat. Nos. 4,238, 599, 4,801,677, 5,173,562, each of which is incorporated by reference herein in its entirety, for further examples of suitable mesogenic units.

Other suitable mesogenic repeating units include those of the following general formula:

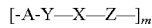

wherein X can be (CH$_2$)$_n$ wherein n is an integer from about 2 to about 10, m can range from about 2 to about 50, Y and Z can each independently be —COO or —CONH or can be a single bond between two carbon atoms, and A can be p-phenylene, 1,4-naphthylene, 2,6-naphthylene or 1,5-naphthylene, monosubstituted phenylene with methyl, chloro or phenyl substitution, —ArCH=CHAr— wherein AR is a phenyl ring, —Ar—COOAr—, —Ar—CONHAr—, or —Ar—OOC—Ar—COO—AR—, etc. For a discussion of such mesogenic repeating units, see U.S. Pat. No. 4,952,334, the entire content of which is incorporated by reference herein.

Another specific example of a suitable aromatic mesogenic repeating unit has the structure —Ar—CO—NH—Ar—NH—CO—Ar—.

Other suitable mesogenic repeating units which can be employed herein are described by Ober et al. in "Liquid Crystal Polymers. V. Thermotropic Polyesters with Either Dyad or Triad Aromatic Ester Mesogenic Units and Flexible Polymethylene Spacers in the Main Chain," *Polymer Journal*, Vol. 14, No. 1, pp. 9-17 (1982) and have the following structure:

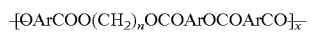

wherein Ar represents phenyl with para-bond sites, n may range from about 2 to about 10, and x can range from about 2 to about 50. These mesogenic units can be characterized as aromatic ester mesogenic units comprising three linearly-aligned aromatic rings.

The type of mesogenic repeating unit represented by the formula above, wherein Ar represents phenyl with para-bond sites, n is an integer of from about 2 to about 10, and x is an integer of from about 5 to about 15, is described in U.S. Pat. No. 5,508,338, the entire content of which is incorporated by reference herein.

Other specific examples of suitable mesogenic repeating units include poly(hydroxynaphthoic acid) (—O—ArAr—CO—, wherein ArAr is two fused benzene rings) and poly(p-phenyleneterephthlate) (—O—Ar—OOC—Ar—CO—).

Another specific example of a suitable LC block employs a combination of hydroxybenzoic and hydroxynaphthoic acid and has repeating units of the formula—[—O—AR—CO—]$_x$—[—O—ArAr—CO—]$_y$— wherein x and y are positive numbers of 1 or more, for instance, x and y may vary independently from about 1 to about 50, and suitably about 1 to about 25. In some embodiments x=y=1 and in other embodiments x≠y. See, for example, U.S. Pat. Nos. 6,552,127, 6,054,537, 5,869,574, 5,767,198 and 5,750,626, each of which is incorporated by reference herein in its entirety.

Another example of a mesogenic unit formed using a combination includes that shown in U.S. Pat. No. 4,912,193, the entire content of which is incorporated by reference herein, employing a combination of p-hydroxy benzoic acid, 4,4'-dihydroxy biphenyl, terephthalic acid, and isophthalic acid. The above lists are intended for illustrative purposes only and not as a limitation on the scope of the present invention.

Mesogen substituted (meth)acrylates, isocyanates, styrenic monomers, and diene monomers such as isoprene and butadiene, can also be employed in the formation of LCP block copolymers as disclosed herein.

Liquid crystal polymers having mesogenic acrylate repeating units find utility herein. One example of an acrylate mesogenic repeating unit which results in a side chain liquid crystal polymer structure is an acrylate repeating unit having the following structure:

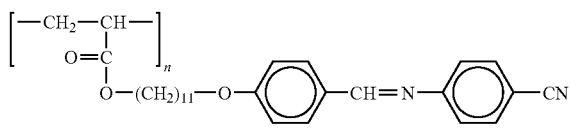

Another example of a suitable (meth)acrylate based mesogenic repeating unit which results in a side chain liquid crystal polymer structure is the following:

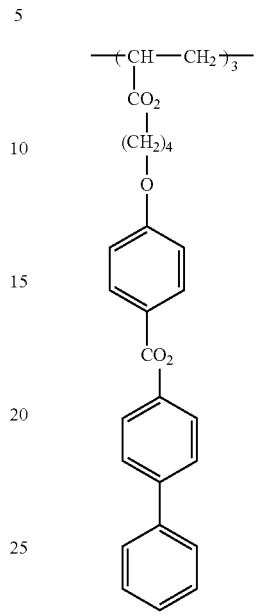

Another example of a mesogenic (meth)acrylate based monomer is 6-(4-methoxy-azobenzene-4'-oxy) hexyl methacylate. This monomer is used in the formation of diblock and triblock copolymers as described in He et al., "Synthesis of side-chain liquid-crystalline homopolymers and triblock copolymers with p-methoxyazobenzene moieties and poly (ethylene glycol) as coil segments by atom transfer radical polymerization (ATRP) and their thermotropic behavior," *Journal of Polymer Science Part A: Polymer Chemistry*, Vol. 41, Issue 18, pages 2854-2864 (2003).

A specific example of an LCP block copolymer formed using a (meth)acrylate monomer modified with mesogenic side chains is disclosed in Gomes et al., "Synthesis of block and graft copolymers containing liquid-crystalline segments," *Polymer International*, Vol. 48, pages 713-722 (1999. In this example, non-LCP block or B block is polystyrene. The LCP block, having a Tg of well below 25° C. forms the soft block of the block copolymer while the polystyrene forms the hard block. The LCP block copolymer can be formed using any of a variety of methods including, for example, chemical modification of poly[styrene-co-tert-butyl acrylate]. In a specific example, poly[styrene-block-(tert-butyl acrylate] copolymer may be synthesized by a living anionic block copolymerization technique, followed by acid-base neutralization of the acrylate with metal alkoxides or metal hydroxides, and subsequent esterification of the ionomer with a hydroxy-terminated mesogen source such as HO(CH$_2$)$_4$OArAr.

LCP block copolymers which find utility herein may be formed with (meth)acrylate based monomer repeating units using controlled free radical polymerization, specifically ATRP techniques, to form LCP block copolymers. See P. Ravi et al., "New water soluble azobenzene-containing diblock copolymer: synthesis and aggregation behavior," *Polymer*, Vol. 46, pp. 137-146 (2005):

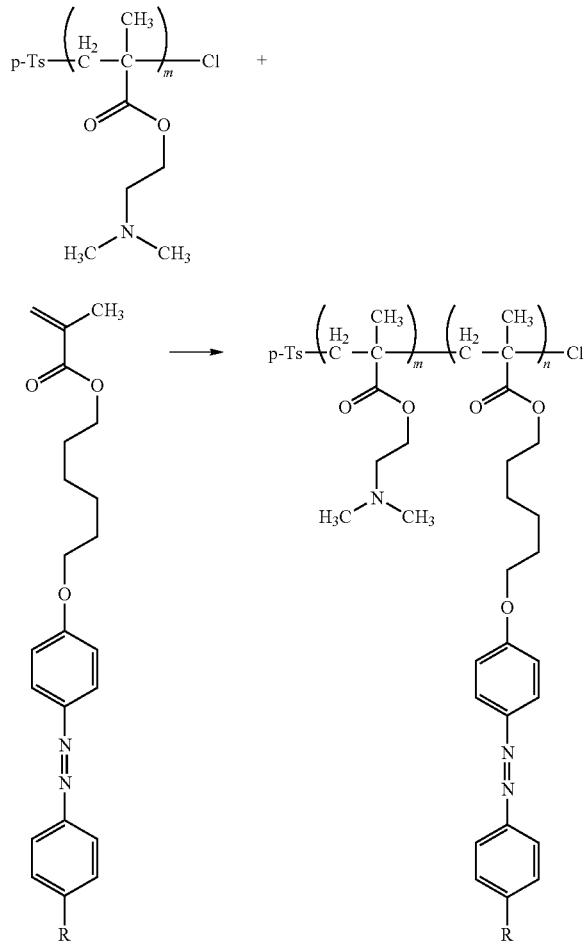

A triblock copolymer formed of rubber midblocks of poly (n-butyl acrylate) and LCP endblocks formed of azobenzene modified (meth)acrylate repeating units in another example of an LCP block copolymer having utility herein. Such polymers are described in Cui et al., "Photoactive Thermoplastic Elastomers of Azobenzene-Containing Triblock Copolymers Prepared through Atom Transfer Radical Polymerization," *Macromolecules*, Vol. 37, pp. 7097-7104 (2004). Particular polymers have the following general structure:

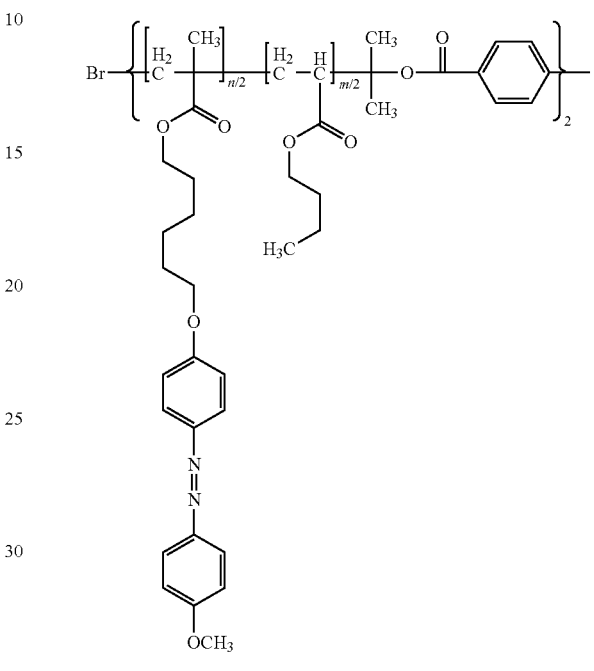

where m and n are positive numbers indicative of the starting ratios of the respective monomers employed in the synthesis of the polymer. An alternative structure which may be employed in the present invention is formed using ATRP techniques and may be found in Han et al., "Synthesis and Characterization of New Liquid-Crystalline Block Copolymers with p-Cyanoazobenzene Moieties and poly(n-butyl acrylate) segments Using Atom-Transfer Radical Polymerization," *Macromolecules*, Vol. 37, pp. 9355-9365 (2004):

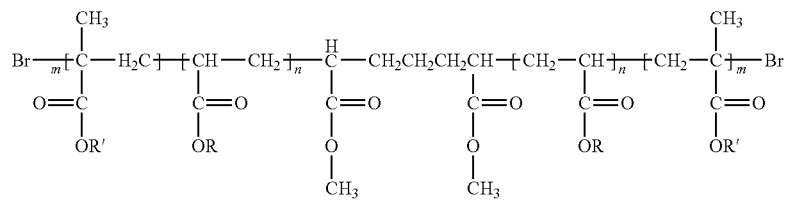

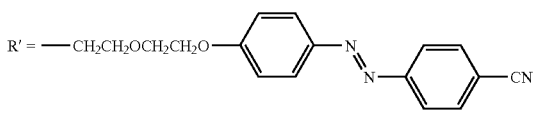

where m and n are positive numbers indicative of the nominal number of repeating units per polymer chain.

Block copolymers having non-LCP polystyrene blocks and mesogen-substituted (meth)acrylate blocks find utility herein and may be prepared by any of a variety of methods including cationic polymerization of styrene, followed by sequential living ionic polymerization of the polyacrylate block. Structure I shown below is described in Yamada et al., "Synthesis of Side-Chain Liquid Crystalline Homopolymers and Block Copolymers with Well-Defined Structures by Living Anionic Polymerization and Their Thermotropic Phase Behavior," *Macromolecules*, Vol. 28, pp. 50-58 (1995). Structure II shown below is a diblock polymer having a non-LCP polystyrene block (B) and a methyl (meth)acrylate LCP block (A) modified with a mesogenic side-chain group. This polymer is described in Yamada et al., "Side-Chain LC Block Copolymers with Well Defined Structures Prepared by Living Anionic Polymerization. 2: Effect of the Glass Transition Temperature of Amorphous Segments on the Phase Behaviour and Structure of the LC Segment," *High Performance Polymers*, Vol. 10(1), pp. 131-138 (1998) and may be prepared using living ionic polymerization techniques.

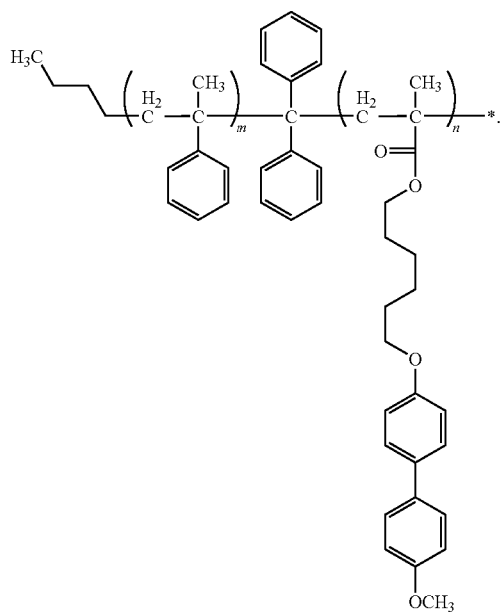

I

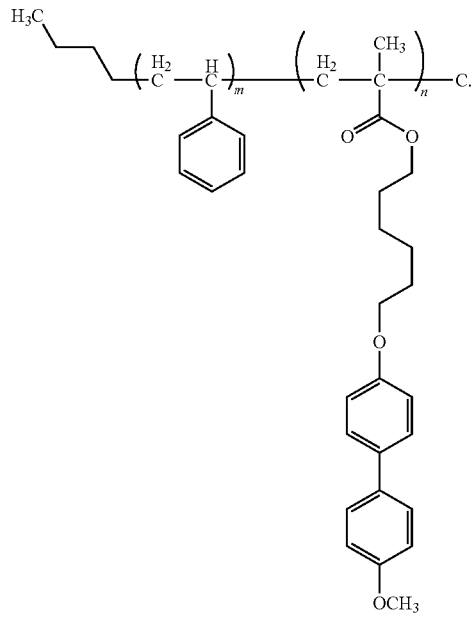

II

Polystyrene-mesogen-substituted acrylate block copolymers can also be prepared using controlled radical reaction schemes such as ATRP, nitroxide-mediated polymerization (NMP) and reverse-addition fragment transfer (RAFT). These reactions schemes can involve sequential building of each polymer block or building the end blocks simultaneously onto a mid-block. Using the first approach, one end of the polymer remains reactive while using the latter approach involved addition polymerization of the LCP end-blocks onto a telechelic mid-block which acts as a difunctional macroinitiator. For example, a chloride-terminated polyisobutylene mid-block prepared by cationic polymerization, can be used as a macroinitiator for mesogen-substituted styrene or acrylate monomers.

Structures III and IV find utility herein and have been prepared using controlled free radical polymerization techniques. Structure III is described in Barbosa et al., "Living tandem free radical polymerization of a liquid crystalline monomer," *Polymer Bulletin*, Vol. 41, pp. 15-20 (1998) and was prepared using NMP techniques. Structure IV shown below is a diblock polymer having a non-LCP polystyrene block (B) and an LCP block (A) of poly(methyl methacrylate) bearing a chiral diphenyl ester mesogenic unit lined in to the backbone by a dodecyloxy spacer. This molecule can be formed by ATRP as described in Hamley et al., "Interplay between Smectic Ordering and Microphase Separation in a Series of Side-Group Liquid-Crystal Block Copolymers," *Macromolecules*, Vol. 37, pp. 4798-4807 (2004).

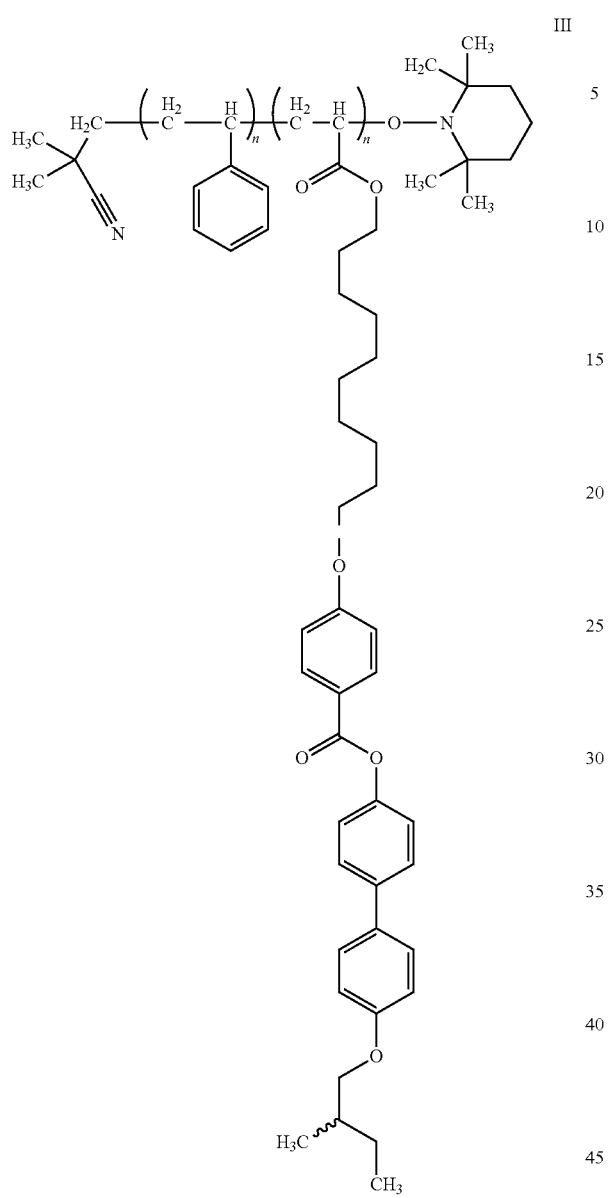 III

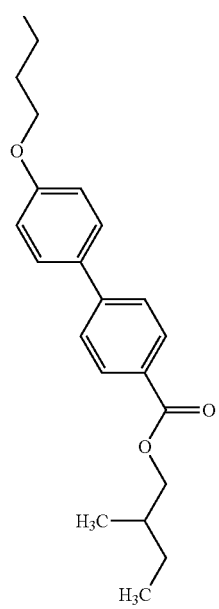

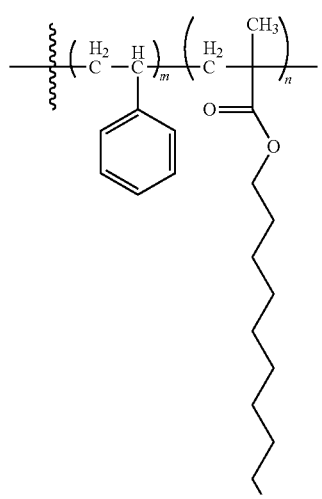 IV where m and n are positive numbers indicative of the starting of the respective monomers employed in the synthesis of the polymer.

Another example of a block copolymer having non-LCP polystyrene midblocks and LCP endblocks formed with (meth)acrylate monomers modified with mesogens of a similar structure to that shown above and also formed by ATRP techniques is the following structure V and is described in Tian et al., "Photocrosslinkable Liquid-Crystalline Block Copolymers with Coumarin Units Synthesized with Atom Transfer Radical Polymerization," *Journal of polymer Science: Part A: Polymer Chemistry*, Vol. 41, pp. 2197-2206 (2003):

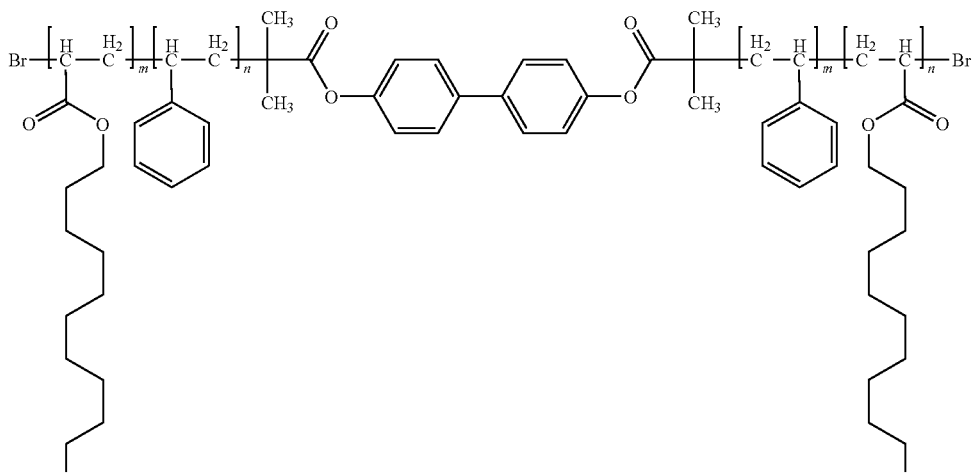

V

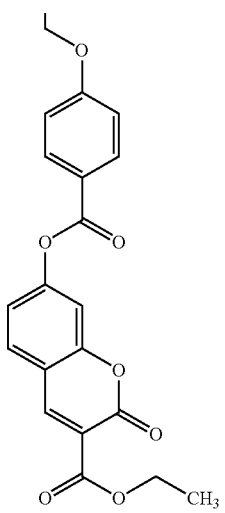
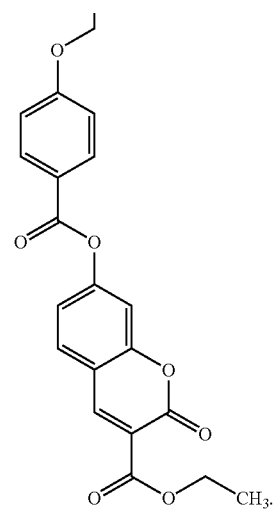

Where m and n are positive numbers indicative of the nominal number of repeating units per polymer chain.

Other examples of LC block copolymers having LCP blocks formed with (meth)acrylate repeating units are disclosed in Hao et al., "Molecular composite materials formed from block copolymers containing a side-chain liquid crystalline segment and an amorphous styrene-alt-maleic anhydride segment," *Polymer*, Vol. 45, pp. 7401-7415 (2004). An example given by Hao et al. is an LC block copolymer formed with a poly[6-[4-4'-methoxyphenyl)phenoxy]hexyl methacrylate] segment (PMM-LC) and a styrene-co-maleic anhydride segment (alternating structure) and may be prepared using RAFT techniques. The reaction to produce PMM-LC is shown below:

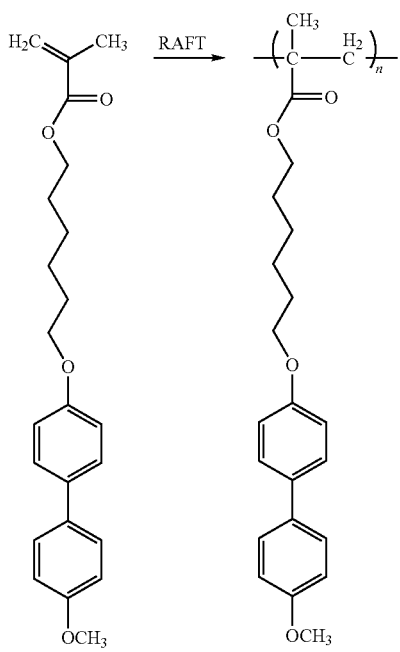

This polymer can then be used to re-initiate styrene/maleic anhydride alternating copolymerization.

Block copolymers having non-LCP polystyrene blocks with the B blocks formed from repeating units other than (meth)acrylate monomers may also be employed herein. For example, see Wan et al., "Nitroxide-mediated 'living' free radical synthesis of novel rod-coil diblock copolymers with polystyrene and mesogen-jacketed liquid crystal polymer segments," *Polymer International*, Vol. 49, pp. 243-247 (2000) wherein an example of a block copolymer having a non-LCP polystyrene block is polystyrene-block-poly{2,5-bis[4-methoxyphenyl)oxycarbonyl]styrene} These polymers are formed using NMP techniques.

LCP blocks having non-LCP polystyrene blocks with a LCP block formed with siloxane repeating units may be employed herein. One example is cyclic trimethyltrivinyl-trisiloxane which is modified with mesogenic side groups. For example, in Moment et al., "Synthesis of polystyrene-polysiloxane side-chain liquid crystalline block copolymers," *Macromolecular Rapid Communications*, Vol. 19, pages 573-579 (1998), mesogens are attached to the siloxane backbone of a polystyrene-polysiloxane side-chain liquid crystal block copolymer following synthesis of the block copolymer. The mesogens may have the following structures:

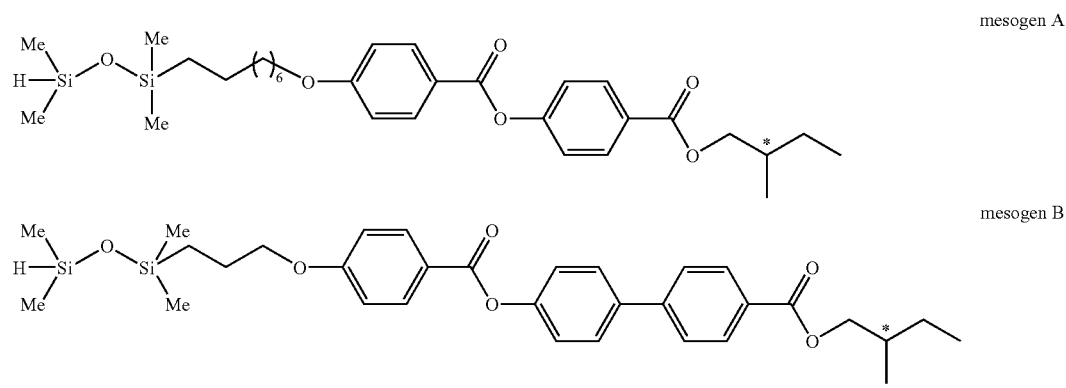

The following polydimethylsiloxane LCP block copolymer also finds utility herein and can be formed using ATRP techniques:

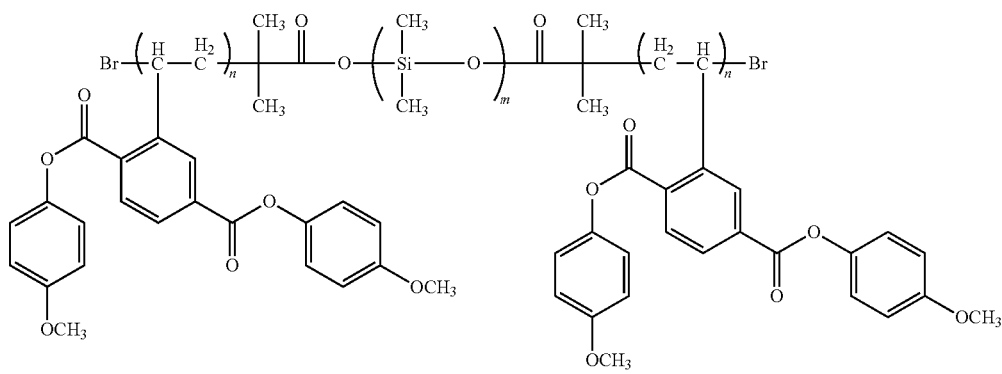

where m and n are positive numbers indicative of the starting ratios of the respective monomers employed in the synthesis of the polymer. See Huan et al., "Synthesis and Properties of Polydimethylsiloxane-Containing Block Copolymers via Living Radical Polymerization," *Journal of polymer Science: Part A: Polymer Chemistry*, Vol. 39, pp. 1833-1842 (2001).

Polymers formed of repeating units of epichlorohydrin wherein the epichlorohydrin is modified with a mesogenic group may be employed in the formation of the LCP block copolymers disclosed herein. Epichlorohydrin polymers are formed using a ring opening polymerization of epichlorohydrin, followed by subsequent substitution of the chloride with a mesogenic group, for example, —CH$_2$O—(CH$_2$)$_n$OArAr═N. Epichlorohydrin monomers can then be added using living ionic polymerization techniques to obtain the LCP block copolymer. See X. Han et al. at 743 for the formation of side-chain liquid crystal poly[1-({[4-cyano-4'-diphenyl)oxy]alkyl}oxy)2,3-epoxypropane] which may be employed as the mesogenic A block in an embodiment of the present invention. Such a polymer may be represented by the formula:

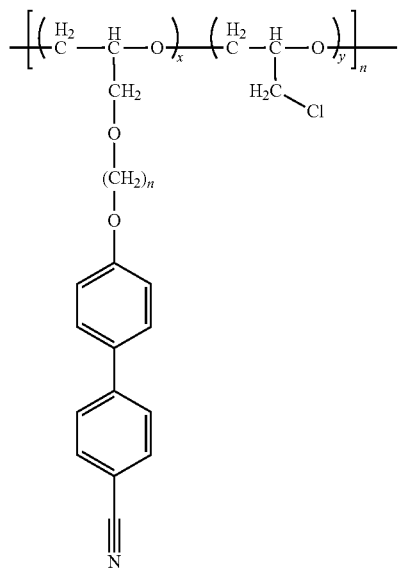

where X and Y are integers. X. Han et al., "Synthesis and Characterization of Side-Chain Liquid Crystalline Poly[1-({[4-cyano-4'-diphenyl)oxy]alkyl}oxy)2,3-epoxypropane]," *Macromolecular Chemistry and Physics* at 743-751. See also M. C. Bignozzi et al., "Liquid Crystal Poly(glycidyl ether)s by Anionic Polymerization and Polymer-Analogous Reaction," *Polymer Journal*, Vol. 31, No. 11-1, pp. 913-919 (1999) wherein the mesogenic group has the structure —OArN═NArO(CH$_2$)$_m$CH$_3$. Such polymers can also be prepared by a sequential ring-opening anionic polymerization of different epoxides one of which has a mesogneic side chain group.

LCP block copolymers having substituted non-LCP polyamide blocks and blocks formed with mesogen-substituted amide repeating units with the following structure can also be prepared via ring opening anionic polymerization:

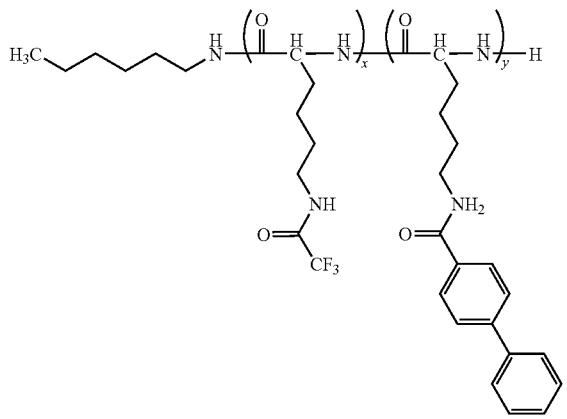

See C. Guillermain et al., "Homopolymer and copolymers of N$^\epsilon$-4-phenylbenzamido-L-lysine and N$^\epsilon$-trifluororacetyl-L-lysine: Synthesis and liquid-crystalline properties," *Macromolecular Chemistry and Physics*, Vol. 203, Issue 10-22, pp. 1346-1356 (2002).

Ionic polymerization techniques lend themselves to the addition of a variety of different monomers to living ionic polymerizations as well. LCP monomer units can be added sequentially to living ionic polymerizations reactions, thereby readily building LCP blocks onto non-LCP mid-block. For example, mesogen-substituted monomers such as acrylates as discussed above, and styrenic monomers, may also be used in a sequential cationic polymerization scheme to yield the desired LCP block copolymer.

Examples of cationically prepared LCP monomer units which can be sequentially added to living ionic polymerizations include, for example, cyclic structures such as 2-methyl-7-oxa-bicyclo[2,2,1]heptane, and polyoxazolines such as those having the following general structure:

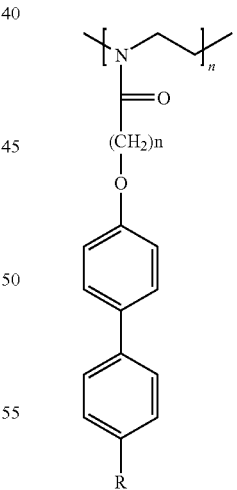

See Rodriguez-Parada et al., "Synthesis and Characterization of Liquid Crystalline Poly(N-acetyethyleneimine)s," *Journal of polymer Science: Part A, Polymer Chemistry*, Vol. 25, 2269-2279 (1987).

Mesogen substituted isocyanates having the following general structure can be polymerized cationically and subsequently added to a non-LCP block of polyisoprene via sequential ionomeric addition:

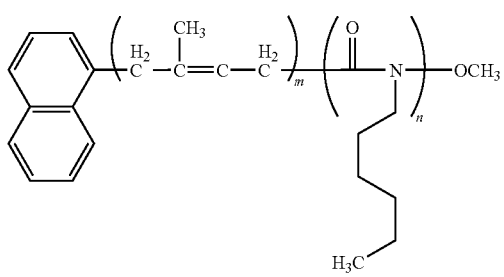

See Jun-Hwan Ahn et al., "Synthesis of well-defined block copolymers of n-hexyl isocyanate with isoprene by living anionic polymerization," *Polymer* 44, pp. 3847-3854 (2003).

Mesogen substituted styrene monomers having the following general structure can be employed to prepare an LCP A block via cationic polymerization techniques which can then be subsequently added to a non-LCP block via sequential ionomeric addition:

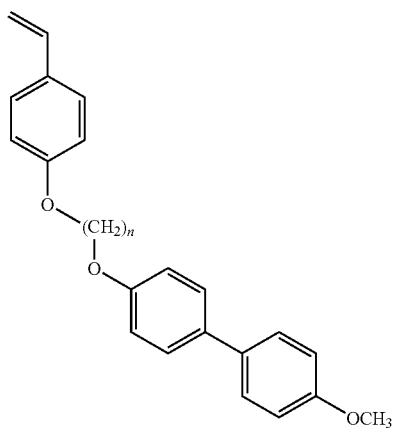

In the block copolymers employed in the invention, the B block may be aliphatic or aromatic. The B block may be formed with any of a variety of suitable repeating units including, but not limited to, olefins, esters, ethers, amides, and siloxane repeating units, for example.

In some embodiments, the B block is aliphatic. In these embodiments, suitably, the B block has less than 10% aromaticity by weight of the B block, more suitably the B block has less than 5% aromaticity by weight of the B block, and most suitably the B block has substantially no aromaticity. This type of block may be a soft block.

In some embodiments, the B block is aromatic. See for example, Gomes et al. at 713 wherein the B or mid block is polystyrene.

Styrenic block copolymers having styrene end-blocks and diene midblocks such as isoprene or butadiene, can be modified with mesogenic side chains to form a liquid crystal block copolymer wherein polystyrene is the non-LCP B block. The styrene-diene block polymers can be synthesized using any known method followed by addition of the mesogenic side chain. Examples are found in Mao et al., "Molecular Design, Synthesis, and Characterization of Liquid Crystal-Coil Diblock Copolymers with Azobenzene Side Groups, *Macromolecules*," Volume 30, pages 2556-2567 (1997), carboxylic acid functionalized azobenzene mesogenic side chains were attached to the isoprene block. One example has the structure HOOC(CH$_5$)OArN=NArC=N. The mesogen was attached via acid chloride coupling by converting the carboxylic acid to the acid chloride, oxalyl chloride prior to addition to the isoprene block in order to improve reaction times. Hydroboration was used to convert pendent double bonds of an isoprene block to hydroxyl groups to which the mesogenic groups were attached via acid chloride coupling.

Modified styrene monomers may be employed for both the formation of the non-LCP block (B) and the LCP block (A). For example, an acetoxystyrene polymer forms the basis for the following LCP block copolymer formed by living free radical polymerization:

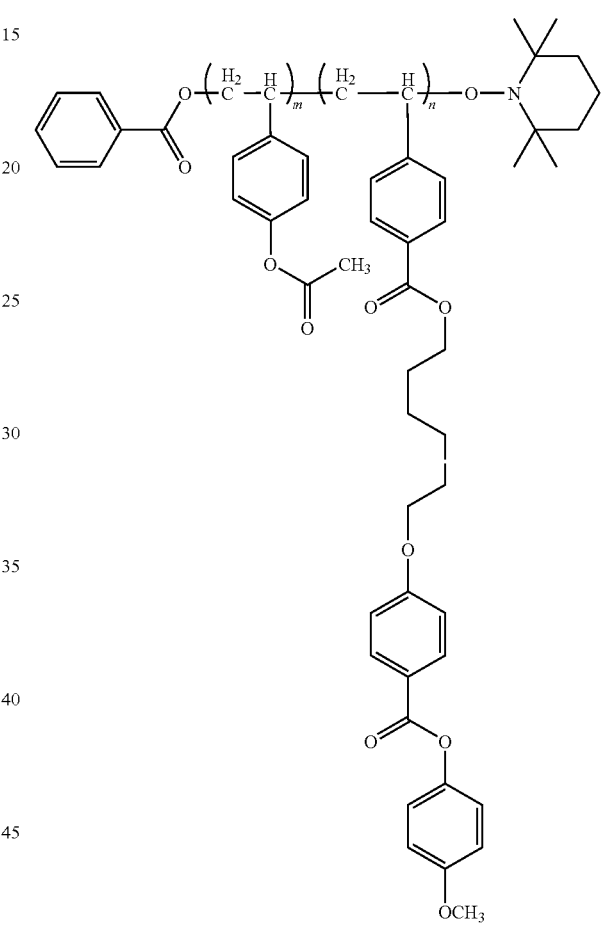

where M and N are integers. See Bignozzi et al., "Liquid crystalline side chain-coil diblock copolymers by living free radical polymerization," *Macromolecular Rapid Communications* Vol. 20, pp. 622-627 (1999).

Another example of a block copolymer of styrene and isoprene modified with mesogen side-chain groups is described in J. Wang et al., "Liquid Crystalline, Semifluorinated Side Group Block Copolymers with Stable Low energy Surfaces: Synthesis, Liquid Crystalline Structure, and Critical Surface Tension," *Macromolecules*, Vol. 30, pp. 1906-1914 (1997). Poly(styrene-b-1,2/3,4-isoprene is first synthesized by anionic polymerization techniques. The base block polymer was hydroborated followed by attachment of semifluorinated side groups by formation of ester linkages between the hydroxy groups and the semifluorinated acid chloride. The block copolymer has the following structure:

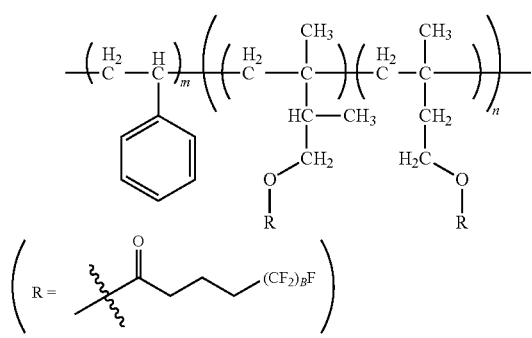

The length of the fluorocarbon side chain determines the ability of the polymer to form a micellular structure. More than six —(CF$_2$)— groups were found to produce micelle structures. Suitably ten fluorocarbon groups are present in the mesogenic side chain for substantially all of the molecules to form a micellular structure. The length of the methylene spacer group was also found to affect micelle formation. With three methylene groups in the spacer, about 80% of the molecules formed micelles. With —(CH$_2$)$_5$— about 30% of the molecules formed micelles and with —(CH$_2$)$_9$— only 20% of the molecules. A sufficiently long spacer group improves the solubility of such molecules in solvent. See Wang et al. at page 1909-1910.

(Meth)acrylate block copolymers modified with fluorocarbon side-chain mesogenic groups find utility herein and may be formed using ATRP as described in Al-Hussein et al., "Nanoordering of Fluorinated Side-Chain Liquid Crystalline/Amorphous Diblock Copolymers, Macromolecules," Vol. 38, pp. 9610-9618 (2005). These polymers have the following structure:

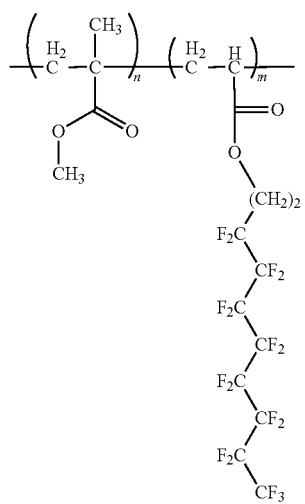

These types of LCP block copolymers also provide a surface having a low surface energy or low coefficient of friction and therefore find utility in also providing lubricity to the medical device. They may be used in the matrix material which forms at least a portion of the block copolymer, or they may also find utility as a coating on the surface(s) of a device.

Multiarm star rod-coil block copolymers may be employed herein. For example, see Chen et al., "Synthesis and Characterization of Novel Mesogen-Jacketed Liquid Crystalline Miktoarm Star Rod-Coil Block Copolymer," *Macromolecular Rapid Communications*, Vol. 27, pp. 51-56 (2006). These multiarm star block copolymers were produced by ATRP of styrene monomers and {2,5-bis[(4-methoxyphenyl)oxycarbonyl]styrene} rigid rod segments. Both three arm rigid rod block copolymers (Chen et al. at 51-56) and four arm rigid rod block copolymers of this type may be employed. See Wang et al., "Synthesis and characterization of four-armed star mesogen-jacketed liquid crystal polymer," *Journal of Polymer Science Part A: Polymer Chemistry*, Vol. 43, pp. 733-741 (2005) for a four armed structure. Also reproduced in *Polymer*, Vol. 45, pp. 3637-3642 (2004).

Another example of a multiarm star block copolymer is a tri-armed star poly(ε-caprolactone)-b-poly{2,5-bis[(4-methoxyphenyl) oxycarbonyl]styrene} [S-(PCL-b-PMPCS)$_3$]. Shi et al., "Synthesis and Characterization of a novel star shaped Rod-Coil Block Copolymer," *Polymer Bulletin*, Vol. 52, pp. 401-408 (2004). Different initiators may be employed such as 1,3,5-(2'-bromo-2'-methylpropionato)benzene and 1,1,1-tris(2-bormo-isobutyryloxymethyl)propane. See Wang et al., "Synthesis of a novel star liquid crystal polymer using trifunctional initiator via atom transfer radical polymerization," *European Polymer Journal*, Vol. 41, pp. 933-940 (2005). Other examples of star block copolymers which may be employed herein are described in He et al., "Synthesis of novel multi-arm star azobenzene side-chain liquid crystalline copolymers with a hyperbranched core," *European Polymer Journal*, Vol. 40, pp. 1759-1765 (2004) and He et al. "Branched Azobenzene Side-Chain Liquid-Crystalline Copolymers Obtained by Self-Condensing ATR Copolymerization," *Macromolecular Rapid Communications*, Vol. 25, pp. 949-953 (2004). The multi-arm block copolymers can be synthesized using ATRP techniques using a multi-functional hyperbranched polyether prepared from poly(3-ethyl-3-(hydroxymethyl)oxetane)(PEHO) and 2-bromo-2-methylproponyl bromide. The liquid crystalline arms were poly[6-(4-methoxy-4''-oxy-azobenzene)hexyl methacrylate].

Multiarm block copolymers may be formed living free radical polymerizations as discussed above, as well as anionic and cationic polymerizations, end-coupling of prepolymers or a combination of strategies.

The B block may also be formed with hydrophilic monomer units. Examples of suitably hydrophilic monomers include, but are not limited to, short chain aliphatic ethers such as polyethylene oxide or polyethylene glycol, polytetramethylene oxide or polytetramethylene glycol diols or dicarboxylic acids containing a metal sulfonate group, oligomers such as polyalkylene glycol copolymerized with other monomers such as aliphatic dicarboxylic acids, hydrophilic acrylates available from Sartomer such as polyethylene glycol diacrylate, acrylamides and N,N-dimethylacrylamide, N-vinylpyrrolidone, etc.

An example of an LCP block copolymer having a hydrophilic B block is described in He et al., "Synthesis of side-chain liquid-crystalline homopolymers and triblock copolymers with p-methoxyazobenzene moieties and poly(ethylene glycol) as coil segments by atom transfer radical polymerization and their thermotropic behavior," *Journal of Polymer Science Part A: Polymer Chemistry*, Vol. 41, Issue 18, pages 2854-2864 (2003). Triblock copolymers, A-B-A, wherein the A block is formed of repeating units of an azobenzene monomer, 6-(4-methoxy-azobenzene-4'oxy) hexyl methacrylate and the B block is formed of repeating units of polyethylene glycol were synthesized using atom transfer radial polymerization (ATRP). See also He et al., "Synthesis of Side Chain Liquid Crystal-Coil Diblock Copolymers with p-Methoxyazobenzene Side Groups by Atom-Transfer Radical Polymerization (structure V)", *Polymer Chemistry*, Vol. 41, 2854-2864 (2003) and Tian et al., "Synthesis, Nanostructures, and Functionality of Amphiphilic Liquid Crystalline Block Copolymers with Azobenzene Moieties," *Macromolecules*, Vol. 35, pp. 3739-3747 (2002) (structure VI) below:

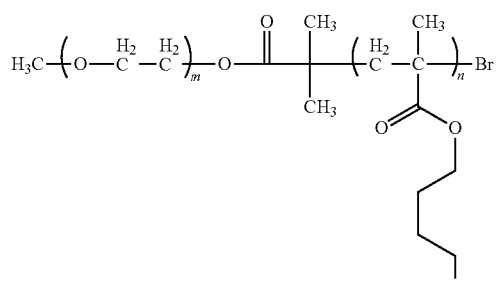

V

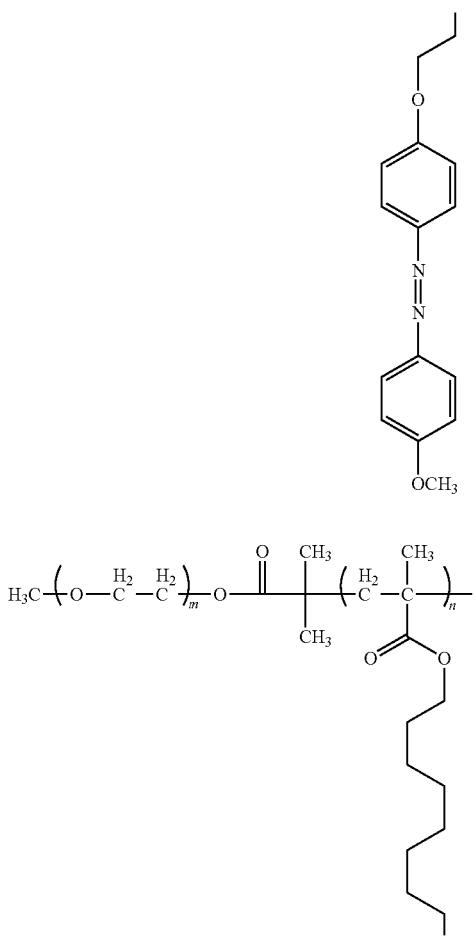

VI

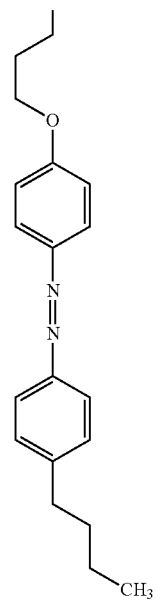

Another example is poly(11-(4'-cyanophenyl-4"-phenoxy) undecyl methacrylate) with polyethylene glycol segments. See He et al., "Synthesis of side group liquid crystal-coil triblock copolymers with cyanodiphenyl moieties and PEG as coil segments by atom-transfer radical polymerization and their thermotropic phase behavior," *Polymer Bulletin*, Vol. 48, pp. 337-344 (2002).

The above are intended for illustrative purposes only, and not as a limitation on the scope of the present invention.

The A block may have anywhere from about 2 to about 50 repeating units, and more suitably about 2 to about 25 repeating units, and the B block may have anywhere from about 2 to about 25 repeating units, and suitably about 2 to about 10 repeating units.

In some embodiments the block copolymer further has a C block, the C block is a mesogenic block different than the mesogenic A block. The mesogenic units of the C block may be selected from those mesogenic repeating units discussed as useful in forming the A block. However, in a liquid crystal polymer having both an A block and a C block, the C block is formed from different mesogenic repeating units than those of the A block. For example, in one embodiment, the A block of the liquid crystal block copolymer is a polyamide segment and the C block is a polyester segment formed using aromatic hydroxycarboxylic acids, for example. Examples of suitable mesogenic units for formation of the polyamide A block structure include, for example, This portion of the liquid crystal block copolymer can be made by the condensation reaction between HOOC—AR—COOH (benzene-1,4-dicarboxylic acid) and $H_2N$—AR—$NH_2$ (1,4-diaminobenzene) to form the following structure:

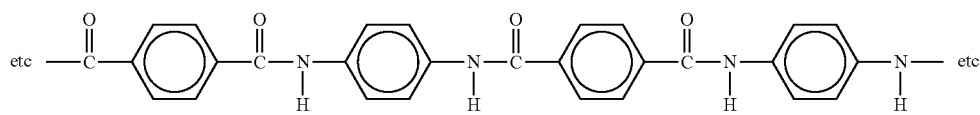

In this embodiment, suitable B blocks may be formed by condensation of hexanedioic acid and hexamethylenediamine (nylon 6,6), ring opening polymerization of caprolactam (nylon 6) or ring opening polymerization of laurolactam (nylon 12), for example.

Nylon 6 (polycaprolactam) is not a condensation polymer, but rather is formed by the ring opening polymerization of caprolactam monomers.

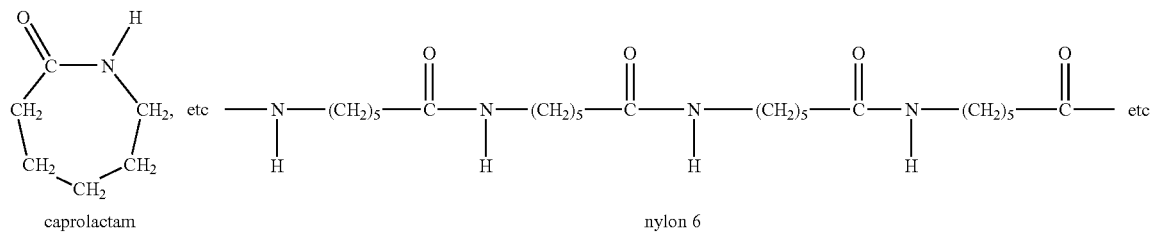

caprolactam nylon 6

Nylon 6,6, on the other hand, is formed by condensation between hexanedioic acid (adipic acid) and 1,6-diaminohexane (hexamethylenediamine): repeating unit:

Hexanedioyl dichloride may be used in place of hexanedioic acid.

The above list is intended for illustrative purposes only, and not as a limitation on the scope of the present invention.

The liquid crystal polyester A block, the nylon B block and the liquid crystal polyamide C block can be connected via conventional condensation reactions.

The C block may also have anywhere from about 2 to about 50 repeating units, and more suitably anywhere from about 2 to about 25 repeating units.

In some embodiments, the A block is from about 30% to about 95%, more suitably about 50% to about 95%, and even more suitably about 70% to about 90%, by weight of the block copolymer and the B block is about 5% to about 70% by weight of the block copolymer, and more suitably from about 5% to about 50% by weight of the block copolymer, more suitably, the B block is about 10% to about 30% by weight of the block copolymer. In some embodiments, the B block or soft segment is about 10% or less by weight of the LC block copolymer.

Any suitable method of polymerization may be employed depending on the monomers, oligomers, or polymers which are employed. Most commonly, the polymerization can be accomplished via condensation reactions which are achieved through reacting molecules incorporating alcohol, amine or carboxylic acid (or other derivative) functional groups. An ether, amide, or ester linkage is formed and a small molecule, commonly water, is released. Thus, only a part of the monomer becomes part of the polymer.

Example

In a specific example 4-hydroxy-2-benzoic acid (HBA) may be acetylized to 4-acetoxybenzoic acid (ABA) with acetic anhydride as the solvent in the presence of a catalytic amount of sodium acetate in the manner of Chen et al, "Synthesis and properties of liquid crystalline polymers with low $T_m$ and broad mesophase temperature ranges," *Polymer,* 46 (2005) 8624-8633. Still following the method of Chen et al, ABA then may be reacted with 1,4-butanediol (BDO) in a molar ratio of about 1:3 and $Sb_2O_3$ catalyst in an amount of about 300 ppm to produce the ester ABA-BDO-ABA.

Polymerization is then accomplished by adding a mixture of the ester ABA-TMG-ABA, terephthalic acid (TPA), a nylon 6 polymer terminated on both ends with acid groups (Ny6) and 250-300 ppm of $Sb_2O_3$ or $Ti(OBu)_4$ catalysts to a flask with a nitrogen purge using a molar ratio of the ester to TPA to Ny6 dicarboxylic acid of 1.0:0.67:0.33. The nitrogen outlet is equipped with a distillation column with vacuum. The mixture is heated at melt for about 5 hours at a temperature of about 200° C. to about 250° C., depending on the temperature necessary to melt the mixture. Thermal stabilizers and antioxidants such as Irganox® 1010 available from Ciba-Geigy are used added to inhibit decomposition. The mixture is stirred, for instance at 200 rpm once the melt temperature has been reached. The nitrogen flow is regulated to prevent evaporation of reactants. After about 3-5 hours the temperature is gradually increased to about 280° C. and the acetic acid produced by condensation is removed by distillation. When no more distillate is observed a vacuum of about 10 torr is applied for 2-3 hours and then the vacuum is reduced to 1-2 torr and the mixture stirred continuously for an additional 4 hrs, all the while maintaining the temperature at about 280° C. The product is then allowed to cool. Monomers and oligomers may be removed by Soxhlet extraction using acetone.

The resultant polymer is an A-B-A block copolymer having a structure of [(ABA-BDO-ABA-TPA)$_x$ABA-BDO-ABA]-Ny6-[ABA-BDO-ABA-(TPA-ABA-BDO-ABA)$_y$].

In modifications of the above equivalent amounts of ethylene glycol or 1,3 propane diol may be substituted for 1,4-butanediol, 6-hydroxy-2-naphthoic acid may be substituted for 4-hydroxy benzoic acid, 2,6-naphthalene dicarboxylic acid may be substituted for TPA, and/or other diacid terminated nylon polymers such as nylon 6,10 or nylon 9,12, may be substituted for the nylon 6 polymer. An A-B diblock copolymer may be synthesized in a similar manner using a mono-acid terminated nylon polymer such as nylon 12, in place of the nylon 6 diacid. Furthermore the relative ratio of short diacid to acid terminated nylon can be varied over a very wide range for instance from about 1:10 to about 1:10 on an acid equivalents basis.

The liquid crystal block copolymer of the invention may itself be employed in the formation of medical devices or components thereof, or, the liquid crystal block copolymer may be blended with another polymer or polymers. In the latter case, suitably, the polymer and the B block may be selected so as to be compatible with one another. Compatibility, as used herein, refers to compatibility on both the macroscopic and microscopic, i.e. molecular, scale. Thus, compatibility on a macroscopic scale, may refer to those polymer blends which do not exhibit gross phase separation.

In polymer mixtures, the matrix polymer may interact strongly with the LC block copolymer or one block of the LC block copolymer, thus providing desirable polymer properties.

In mixtures wherein the LC block copolymer is blended with other polymers, at least one other polymer of the blend, may be selected from those polymers which are non-liquid crystal polymers. Examples of suitable polymers which may be used for blending with the LC block copolymer described herein include, but are not limited to, polyesters and copolyesters, polyamides, polyethers, polyimides, polyolefins and silicones, for example. These polymers are intended for illustrative purposes only, and not as a limitation on the scope of the present invention.

Specific examples of suitable polymers which may be employed in a blend include polyamide elastomers such as those sold under the tradename of PEBAX® available from Arkema, headquarters in Paris, France, and polyester elastomers such as those sold under the name of HYTREL® available from DuPont in Dover, Del. are also suitable for use.

For example, if the liquid crystal block copolymer is blended with a poly(ether-block-amide) copolymer having an $(AB)_n$ block copolymer structure wherein the A block is nylon and the B block is polytetramethylene oxide, a suitable LC block copolymer B block may include amide repeating units or a polytetramethylene oxide structure. The block may suitably be less than about 50% by weight of the LC block copolymer, more suitably about 30% by weight or less of the LC block copolymer and most suitably about 10% by weight or less of the LC block copolymer.

The tensile strength of a typical poly(ether-block-amide) thermoplastic elastomer of the type described above has tensile strength of about 10,000 psi and DSC melting point of about 174° C.

Suitably, the LC block copolymer, to act as a reinforcing material in such a polymer blend, has a tensile strength of greater than about 10,000 psi, for example, greater than about 12,000 psi, more suitably greater than about 20,000 psi and most suitably greater than about 30,000 psi.

Thus, it is desirable to select the LC block copolymer structure so that it has a strong interaction with the thermoplastic elastomer to achieve mechanical strength enhancement through effective load/force transferring.

It is also desirable that the LC block copolymer have a melting point within a thermoplastic processing window of less than the thermal degradation temperature of the thermoplastic elastomer. In the case where the thermoplastic elastomer is poly(ether-block-amide), for example, the melting point range is suitably less than about 240° C. Extrusion/coextrusion is an example of a suitable method to process such thermoplastic materials.

The above example is intended for illustrative purposes only, and not as a limitation on the scope of the invention. Other polymers are known to those of skill in the art and may also be employed herein.

If a blend of polymers is employed, the amount of LC block copolymer is suitably about 75% or less and more suitably about 50% or less. The amount of LC block copolymer employed may be from about 5% to about 75% and more suitably about 5% to about 50% and even more suitably about 10% to about 30%.

The at least one second polymer or blend of polymers may be employed from about 25% to about 95%, more suitably about 50% to about 95% and even more suitably about 70% to about 90%.

The present compositions may be employed in the manufacture of any medical device or component thereof which is suitably formed from polymer compositions. Examples include catheter assemblies used in diagnosing and treating diseases such as vascular diseases.

The present invention finds utility in the manufacture of expandable medical balloons, particularly those employed in the cardiovascular system wherein the balloon size is very small.

Balloon formation is known in the art. In some processes, a tube of polymer material is extruded and then expanded radially and axially. Balloon formation is described in U.S. Pat. No. 4,490,421 and in commonly assigned U.S. Pat. No. 6,024,722, both of which are incorporated by reference herein in their entirety. Of course, other processes are known and may be employed in the present invention.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A medical device, at least a portion of said device formed from a polymer composition comprising at least one liquid crystal block copolymer having at least one A block and at least one B block and wherein
the A block is a liquid crystal polymer block formed from repeating units comprising mesogenic groups, each of said mesogenic groups comprises at least two aromatic rings, the liquid crystal polymer block is a side chain liquid crystal polymer block; and
the B block is a non-liquid crystal polymer block.

2. The medical device of claim 1 wherein the liquid crystal block copolymer is selected from the group consisting of those polymers having the general formula A-B diblock, $(A-B)_n$ wherein n is 1 to 20, $A(B-A)_n$ where n is 2 to 20, $B(A-B)_n$ where n is 2 to 20, A-B-A triblock, B-A-B triblock, A-B-A-B-A pentablock, multiblock copolymers, linear tetrablock copolymers, random block copolymers and random alternating block copolymers, radial star block copolymers, H-type branched block copolymers, T-type branched block copolymers, combs, brushes, dendrons and mixtures thereof.

3. The medical device of claim 1 wherein said block copolymer further comprises a mesogenic block C different than the A block and said block copolymer has a structure which is selected from the group consisting of $B-(A-B—C)_n$—B wherein n is 3 to 20, A-B—C triblock, A-C—B triblock, and A-B—C random block.

4. The medical device of claim 1 wherein said mesogenic groups comprise fluorinated side-chain groups of at least —$(CF_2)_8$— wherein said —$(CF_2)_8$— is connected to a spacer having three methylene groups or less.

5. The medical device of claim 1 wherein said B block comprises aromaticity.

6. The medical device of claim 5 wherein said B block is styrene.

7. The medical device of claim 1 wherein said A block is formed from repeating units wherein the repeating unit comprises a monomer selected from the group consisting of siloxanes, (meth)acrylates, isocyanates, styrenic monomers, and diene monomers.

8. The medical device of claim 7 wherein said monomer comprises side chain mesogenic groups.

9. The medical device of claim 1 wherein the A block is formed from repeating units wherein the repeating units comprises a (meth)acrylate monomer modified with mesogenic side chain groups and the B block comprises styrene.

10. The medical device of claim 1 wherein the polymer composition further comprises at least one polymer selected from the group consisting of polyamides, polyesters, polyethers, polyolefins, polyimides, block copolymers comprising at least one polyolefin, polyester, polyether, polyamide, and/or polyimide segment, silicones, and mixtures thereof and mixtures thereof.

11. The medical device of claim 1 wherein said liquid crystal block copolymer comprises about 50% to about 95% by weight of said A block and about 5% to about 50% by weight of said B block.

12. The medical device of claim 1 wherein said medical device is a catheter assembly comprising at least one shaft or shaft assembly, and said at least a portion of said medical device formed from said polymer composition is said at least one shaft or shaft assembly.

13. The medical device of claim 1 wherein the medical device is an inflatable medical balloon.

14. The medical device of claim 13 wherein said balloon is mounted on a catheter.

15. The medical device of claim 13 further in combination with a stent.

16. The medical device of claim 1 wherein said block copolymer further includes a C block, the C block comprises mesogenic repeating units, the mesogenic repeating units are different than those of the A block.

17. A medical device, at least a portion of said device formed from a polymer composition comprising at least one liquid crystal block copolymer having at least one A block and at least one B block and wherein
the A block is a liquid crystal polymer block formed from repeating units comprising mesogenic groups; and
the B block comprises aromaticity.

18. An expandable medical balloon formed from a polymeric composition, the polymeric composition comprising:
at least one liquid crystal block copolymer having at least one A block formed from repeating units comprising mesogenic groups and the B block is a non-liquid crystal polymer block; and
at least one polymer that is compatible with the B block of said liquid crystal polymer.

19. The expandable medical balloon of claim 18 wherein said B block comprises aromaticity.

20. The expandable medical balloon of claim 19 wherein the polymer composition further comprises at least one polymer selected from the group consisting of polyamides, polyesters, polyethers, polyolefins, polyimides, block copolymers comprising at least one polyolefin, polyester, polyether, polyamide, and/or polyimide segment, silicones, and mixtures thereof and mixtures thereof.

* * * * *